(12) United States Patent
Gaire et al.

(10) Patent No.: US 11,017,533 B2
(45) Date of Patent: May 25, 2021

(54) DISTANCE-BASED TUMOR CLASSIFICATION (71) Applicant: HOFFMANN-LA ROCHE INC., Little Falls, NJ (US)

(72) Inventors: Fabien Gaire, Starnberg (DE); Oliver Grimm, Munich (DE); Hadassah Sumum Sade, Penzberg (DE); Suzana Vega Harring, Starnberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 35 days.

(21) Appl. No.: 16/347,735

(22) PCT Filed: Nov. 2, 2017

(86) PCT No.: PCT/EP2017/078111
§ 371 (c)(1),
(2) Date: May 6, 2019

(87) PCT Pub. No.: WO2018/086985
PCT Pub. Date: May 17, 2018

(65) Prior Publication Data
US 2019/0287249 A1 Sep. 19, 2019

(30) Foreign Application Priority Data
Nov. 10, 2016 (EP) .................... 16198290

(51) Int. Cl.
G06T 7/00 (2017.01)
G06T 7/70 (2017.01)
(Continued)

(52) U.S. Cl.
CPC ........ G06T 7/0016 (2013.01); G06K 9/00147 (2013.01); G06K 9/4642 (2013.01);
(Continued)

(58) Field of Classification Search
CPC ............. G06K 9/00147; G06K 9/4642; G06K 9/6256; G06K 9/6276; G06T 2207/10056;
(Continued)

(56) References Cited

U.S. PATENT DOCUMENTS 5,356,793 A * 10/1994 Koezuka ............ G01N 15/1475
382/133
10,650,929 B1 * 5/2020 Beck ...................... G06N 5/046
(Continued)

FOREIGN PATENT DOCUMENTS

WO WO-2015189264 A1 12/2015

OTHER PUBLICATIONS

Brunker, P. Et al., "RG7386, a Novel Tetravalent FAP-DR5 Antibody, Effectively Triggers FAP-Dependent, Avidity-Driven DR5 Hyper Clustering and Tumor Cell Apoptosis", Molecular Cancer Therapeutics, vol. 15, No. 5, Apr. 1, 2016 (Apr. 1, 2016), pp. 946-957, XP055373631, US.
(Continued)

Primary Examiner — Ian L Lemieux
(74) Attorney, Agent, or Firm — Harness, Dickey & Pierce, P.L.C.

(57) ABSTRACT

The system is configured to receive at least one digital image of a tissue sample of a patient; analyze the at least one received image for identifying tumor cells in a region of the at least one received image; analyze the at least one received image for identifying FAP+ areas in the region, each FAP+ area being a pixel blob representing one or more cells express the fibroblast activation protein—"FAP"; analyze the at least one received image for identifying distances between the identified tumor cells and their respective nearest FAP+ area; computing a proximity measure as a function of the identified distances; process the proximity measure by a classifier for generating a classification result,
(Continued)

the classification result indicating if the tumor of the patient can be treated by a drug or drug-component that binds to FAP; and output the classification result.

17 Claims, 5 Drawing Sheets

(51) Int. Cl.
*G16H 50/70* (2018.01)
*G16H 50/20* (2018.01)
*G06K 9/00* (2006.01)
*G06K 9/46* (2006.01)
*G06K 9/62* (2006.01)

(52) U.S. Cl.
CPC ......... *G06K 9/6256* (2013.01); *G06K 9/6276* (2013.01); *G06T 7/0012* (2013.01); *G06T 7/70* (2017.01); *G16H 50/20* (2018.01); *G16H 50/70* (2018.01); *G06T 2207/10056* (2013.01); *G06T 2207/30024* (2013.01); *G06T 2207/30096* (2013.01)

(58) Field of Classification Search
CPC . G06T 2207/30024; G06T 2207/30096; G06T 7/0012; G06T 7/0016; G06T 7/70; G16H 50/20; G16H 50/70
See application file for complete search history.

(56) References Cited

U.S. PATENT DOCUMENTS

| | | | | |
|---|---|---|---|---|
| 2006/0014137 | A1* | 1/2006 | Ghosh | G01N 33/5029 435/4 |
| 2010/0184093 | A1* | 7/2010 | Donovan | G16H 50/50 435/7.21 |
| 2012/0245089 | A1* | 9/2012 | Trieu | G01N 33/574 514/15.2 |
| 2013/0338016 | A1 | 12/2013 | McDonough et al. | |
| 2014/0024553 | A1* | 1/2014 | Michalek | G06F 19/00 506/9 |
| 2015/0003716 | A1* | 1/2015 | Lloyd | G06K 9/00147 382/133 |
| 2016/0314580 | A1* | 10/2016 | Lloyd | G06T 7/0012 |
| 2017/0193660 | A1* | 7/2017 | Schmidt | G06T 7/40 |
| 2018/0239949 | A1* | 8/2018 | Chander | G06N 20/20 |
| 2019/0113423 | A1* | 4/2019 | Goodman | G06T 7/0014 |
| 2019/0127805 | A1* | 5/2019 | El-Helali | G16H 50/30 |
| 2020/0024669 | A1* | 1/2020 | Spetzler | G16H 50/20 |

OTHER PUBLICATIONS

Notification Concerning Submission, Obtention or Transmittal of Priority Document (PCT/IB/304); for International PCT Application No. PCT/EP/2017/078111 which has an International Filing Date of Nov. 10, 2016.

Notification of Transmittal of the International Search Report and the Written Opinion of the International Searching Authority, or the Declaration (PCT/ISA/220) for International PCT Application No. PCT/EP/2017/078111 which has an International Filing Date of Nov. 10, 2016.

International Search Report (PCT/ISA/210) for International PCT Application No. PCT/EP/2017/078111 which has an International Filing Date of Nov. 10, 2016.

The Written Opinion of the International Search Report (PCT/ISA/237) for International PCT Application No. PCT/EP/2017/078111 which has an International Filing Date of Nov. 10, 2016.

International Preliminary Report on Patentability and Written Opinion dated May 23, 2019, Issued in corresponding PCT Application No. PCT/EP2017/078111.

* cited by examiner

DISTANCE-BASED TUMOR CLASSIFICATION

CROSS-REFERENCE TO RELATED APPLICATIONS

This application is a national phase under 35 U.S.C. § 371 of PCT International Application No. PCT/EP2017/078611 which has an international filing date of Nov. 2, 2017, which claims priority to European Application No. 16198290.5, filed Nov. 10, 2016, the entire contents of each of which are hereby incorporated by reference.

FIELD OF THE INVENTION

The invention relates to the field of image analysis, and more particularly to the field of image-based tumor classification.

BACKGROUND AND RELATED ART

Dysregulated cellular apoptosis and resistance to cell death are important indicators for disease progression. Drugs have been designed for overcoming the apoptosis dysregulations in tumor cells by activating the extrinsic apoptotic pathway. For example, Peter Brünker et al. in Mol Cancer Ther, 15(5), 946-57, 2016 AACR describes a regulatory pathway that is strongly dependent on death receptor (DR) hyperclustering on the cell surface. A bispecific antibody (BsAb) was engineered which simultaneously targets the fibroblast-activation protein (FAP) expressed on cancer-associated fibroblasts on the one hand and DR5 expressed on tumor cells on the other hand. The antibody was able to trigger potent tumor cell apoptosis in vitro and in vivo in preclinical tumor models with FAP-positive fibroblasts and was able to trigger substantial tumor regression in patient-derived xenograft models.

In general, the response of cancer cells to chemotherapeutic and other drugs depends on many different factors and is often unpredictable. For example, p53 mutation renders HCT116 colon carcinoma cells more sensitive to adriamycin and radiation but less sensitive to 5-fluorouracil (Watson A J M, apoptosis and colorectal cancer, 2004, 53(11):1701-1709, doi:10.1136/gut, 2004, 052704). Cancer treatments often have severe side effects and should only be conducted if the expected repressive effect on the tumor justifies the adverse side effects. In particular, prescribing cancer drugs for patients who will not benefit from a drug but nevertheless may suffer from the side effects should be avoided.

SUMMARY

It is an objective of the present invention to provide an improved method and image analysis system for classifying tumors as specified in the independent claims. Embodiments of the invention are given in the dependent claims. Embodiments of the present invention can be freely combined with each other if they are not mutually exclusive.

In one aspect, the invention relates to an image analysis method for tumor classification. The method comprises:
  receiving, by an image analysis system, at least one digital image of a tissue sample of a patient;
  analyzing, by the image analysis system, the at least one received image for identifying tumor cells in a region of the at least one received image;
  analyzing, by the image analysis system, the at least one received image for identifying FAP+ areas in said region; each FAP+ area is a pixel blob representing one or more cells expressing the fibroblast activation protein—"FAP";
  analyzing, by the image analysis system, the at least one received image for identifying distances between the identified tumor cells and their respective nearest FAP+ area;
  computing, by the image analysis system, a proximity measure as a function of the identified distances;
  processing the proximity measure by a classifier for generating a classification result, the classification result indicating if the tumor of the patient can effectively be treated by a drug or drug-component that binds to the FAP protein; and
  outputting, by the image analysis system, the classification result.

For example, the outputting may comprise storing the result in a storage medium and/or displaying the classification result on a display device. The "region" may be the whole image of a whole slide or may be a field of view ("FOV") within said image.

Said features may be advantageous as a reproducible and accurate method is provided that may allow to predict whether a drug or drug-component that binds to FAP will be effective in treating the tumor or not. It has been observed that cancer associated fibroblasts selectively express the FAP protein and are suitable drug targets (Peter Brünker et al. in Mol Cancer Ther; 15(5); 946-57, 2016 AACR, which is incorporated herewith in its entirety by reference). However, it was formerly not possible to accurately and reproducibly predict whether a patient or test animal would benefit from the drug or not.

In a further beneficial aspect, FAP's selective expression on cancer-associated fibroblasts is used for targeting, via the tumor stroma, the activation of a cytotoxic compound that may restrict tumor progression. This strategy is effective independently of FAP's role in tumor progression because FAP may merely be used as a binding partner of the drug for directing and concentrating the drug in the vicinity of the tumor. The strategy does—at least for some drugs—not depend on the effects of the drug on the activity of the FAP protein and the processes in the fibroblasts.

According to some embodiments, the drug is an agent that overcomes apoptosis dysregulation in tumor cells.

Dysregulated cellular apoptosis and resistance to cell death are hallmarks of neoplastic initiation and tumor progression. Therefore, selective activation of tumor cell apoptosis (but not in normal, healthy cells), in particular the extrinsic apoptotic pathway, may allow to stop or slow down tumor progression. For example, the drug can be an agent, e.g. an agonistic antibody, that activates DR5 or DR4 (death receptor (DR)) hyperclustering on the surface of tumor cells. The drug may be a bispecific antibody (BsAb) which simultaneously targets the FAP protein on cancer-associated fibroblasts in tumor stroma and a DR protein, e.g. DR5, on tumor cells. It is assumed that bivalent binding to both FAP and DR5 leads to avidity-driven hyperclustering of DR5 and subsequently strong induction of apoptosis in tumor cells but not in normal cells. An example for such a drug is RG7386. RG7386 antitumor efficacy is observed to be strictly FAP dependent. In combination with irinotecan or doxorubicin, RG7386-based FAP-DR5 treatment was observed to result in substantial tumor regression in patient-derived xenograft models. Bispecific FAP-death-receptor-antibodies like RG7386, a novel and potent antitumor agent in both mono- and combination therapies, has been observed at least in several patients to overcome limitations of previous DR5 antibodies and represents a promising approach to conquer tumor-associated resistance to apoptosis.

Embodiments of the invention exploit information contained in FAP—tumor cell distance to classify tumor cells according to a predicted a treatment outcome. More specifically, specific proximity measures which may be derived, for example, from distance histograms obtained for a tissue sample of a patient may be used for classifying tumor cells into tumor cells being treatable by a bispecific FAP-DR antibody, in particular RG7386, and tumor cells not being treatable by said bispecific antibody.

Moreover, the proximity measure may provide a reproducible descriptor of tumor-associated FAP patterns which does not depend on subjective criteria of pathologists which may differ significantly in dependence on the pathologist who manually analyzes an image of a tumor tissue sample wherein FAP is selectively stained. Thus, it provides annotations which are better suited for generating and training an accurate, machine-learning based tumor cell classifier than manual annotations.

"Fibroblast-activation protein" (FAP) or "Fibroblast-activation protein alpha" is a homodimeric, singlepass type II membrane protein expressed in reactive stromal fibroblasts of more than 90% of epithelial malignancies, including breast, colorectal, and lung cancers and on malignant mesenchymal cells of bone and soft tissue sarcomas. FAP belongs to the serine protease family and is selectively expressed in reactive stromal fibroblasts of epithelial cancers, granulation tissue of healing wounds, and malignant cells of bone and soft tissue sarcomas. The FAP protein, also known as seprase, belongs to the clan SC proteases, is catalytically active as a 170 kD dimer and has dipeptidase and gelatinase activity. FAP expression is seen on cancer-associated fibroblasts of more than 90% of all human carcinomas. Said fibroblasts play an important role in the development, growth and metastasis of carcinomas. Clinical trials have been done for drugs like Talabostat, an inhibitor of FAP and related enzymes, Fibroblasts are associated with cancer cells at all stages of cancer progression. Their production of growth factors, chemokines and extracellular matrix facilitates the angiogenic recruitment of endothelial cells and pericytes. Fibroblasts are therefore a key determinant in the malignant progression of cancer and represent an important target for cancer therapies.

"Carcinoma associated fibroblasts" (CAFs), also referred to as "cancer associated fibroblasts" as used herein are a heterogenous group of fibroblasts, in particular fibroblasts within the tumor stroma, whose function is pirated by cancer cells and redirected toward carcinogenesis. These cells are usually derived from the normal fibroblasts in the surrounding stroma but can also come from pericytes, smooth muscle cells, fibrocytes, mesenchymal stem cells (MSCs), or via epithelial-mesenchymal transition (EMT) or endothelial-mesenchymal transition (EndMT). Unlike their normal counterparts, CAFs do not retard cancer growth in vitro. CAFs perform several functions that support tumor growth, such as secreting vascular endothelial growth factor (VEGF), fibroblast growth factors (FGFs), platelet-derived growth factor (PDGF), and other pro-angiogenic signals to induce angiogenesis. CAFs can also secrete transforming growth factor beta (TGF-β), which is associated with EMT, a process by which cancer cells can metastasize, and is associated with inhibiting cytotoxic T cells and natural killer T cells. As fibroblasts, CAFs are able to rework the ECM to include more paracrine survival signals such as IGF-1 and IGF-2, thus promoting survival of the surrounding cancer cells. CAFs are also associated with the Reverse Warburg Effect where the CAFs perform aerobic glycolysis and feed lactate to the cancer cells.

A "tumor" or "neoplasm" as used herein is an abnormal growth of tissue, and when also forming a mass is commonly referred to as a tumor. This abnormal growth usually but not always forms a mass.

A "proximity measure" is a data value computed from a plurality of minimum tumor cell—FAP+ area distances. For example, it can be a numerical data value, e.g. a fraction or "ratio" (a value between 0 and 1) of different groups of distances or a slope of a line connecting histogram bins or a data value derived therefrom. The proximity measure may indicate whether the majority of tumor cell—FAP+ area distances examined is shorter than a predefined distance threshold, e.g. the physiologically effective distance of a drug having bound to a FAP protein of a cancer-associated fibroblast.

An "image analysis system" as used herein is an electronic system, e.g. a computer, configured for extracting meaningful information from digital images by means of digital image processing techniques. Image analysis tasks can comprise color deconvolution, connected component analysis and/or edge detection for identifying cells, for identifying the type of the cells (tumor or stroma cell, FAP+ fibroblasts, etc.) and distance measurements.

Without the intention to be bound by any theory, it is assumed that drugs targeting the FAP protein that is selectively expressed by cancer-associated fibroblasts can be used to guide the drug to a region lying in sufficient spatial proximity of the tumor, thereby allowing the drug to become effective. Applicant observed that the role of FAP in carcinogenesis depends on the context, in particular on the tumor microenvironment and the distance between the FAP+ fibroblasts and the nearest tumor cells. By performing an image analysis for automatically determining a proximity measure being indicative of the distance of the tumor cells and their nearest FAP+ area, a quick, reproducible and reliable prediction of the efficacy of an anti-tumor drug that binds to the FAP protein can be computed.

In a further beneficial advantage, choosing anti-tumor drugs which bind to the FAP protein, i.e., a protein expressed on cancer-associated fibroblasts rather than tumor cells, may be beneficial as the protein expression profile of said fibroblasts is comparatively stable compared to the protein expression profile of tumor cells. This is because tumor cells, in particular in later stages, are genetically unstable. Thus, measuring the distance of the tumor cells and their nearest FAP+ areas (which correspond to clusters of one or more CAFs) may provide a proximity measure that is a more accurate and reproducible predictor of the efficacy of a drug against the tumor than the presence of a particular tumor marker on the surface of the tumor cells themselves.

Using a drug that targets FAP, e.g. drugs which have at least a binding site that binds to the FAP protein, may allow to "encapsulate" an anti-tumor drug as the tumor is surrounded by fibroblasts which "attract" and locally concentrate the drug. Thus, the total amount of the drug/its concentration in the blood can be comparatively low. This may decrease side effects.

It has been observed that computing a proximity measure and using it as a predictor for drug efficacy as described herein for embodiments of the invention is highly accurate and reproducible, presumably because the binding of the drug to the cancer-associated fibroblasts ensures that the drugs are concentrated and take effect in close spatial proximity to the tumor.

According to embodiments, the tissue sample is a whole slide tissue sample and the digital image is a whole slide image. Using the approach for whole slide images may be advantageous as the distances can be identified efficiently in a short time for a plurality of tumor cells. Thus, many tumor cells in a slide and corresponding image can be classified quickly and the method may also be used in slide scanning systems for performing a mass classification operation of the tumor cells depicted in many different tissue slides of many different patients.

The classifier can be, for example, a rule-based classifier, a support vector machine, a neural network, a random forest or other type of classifier. Preferentially, the classifier is a machine learning algorithm that was trained on a plurality of training images comprising tumor cell pixel blobs having been annotated as treatable and non-treatable tumor cells based on empirical data obtained from at least two cohorts of patients.

According to embodiments, the identification of the tumor cells comprises identifying proliferating non-lymphoid cells and using said identified cells as the tumor cells. For example, one or more biomarkers such as KI67 or PCNA (proliferation markers) and CD3 (an immune cell marker) may be used as targets for respective fluorescent or brightfield stains in a staining assay. One or more (fluorescence or brightfield) images of a stained tumor tissue slide are captured by an image capturing device, e.g. a fluorescent or brightfield microscope or a slide scanning device, and the images are analyzed for determining the presence and absence of the one or more biomarkers used for identifying tumor cells. For example, KI67+/CD3− cells are identified as proliferating non-lymphoid cells and may be identified as tumor cells.

According to other embodiments, the identification of the tumor cells comprises identifying cells expressing or over-expressing a set of one or more tumor-specific biomarkers and using said identified cells as the tumor cells. For example, the one or more tumor-specific biomarkers can be a particular cytokeratin ("CK+") or a set of two or more cytokeratins. Often, tumor cells of a particular tumor type show a tumor type specific cytokeratin expression profile and the profile can be used for identifying the tumor type. Cytokeratins are proteins of keratin-containing intermediate filaments found in the intracytoplasmic cytoskeleton of epithelial tissue. For example, basic cytokeratins CK1, CK2, CK3, CK4, CK5, CK6, CK7, CK8 and acidic cytokeratins CK9, CK10, CK12, CK13, CK14, CK16, CK17, CK18, CK19, and CK20 are known. Expression of these cytokeratins is frequently organ or tissue specific. Therefore, cytokeratin expression profiles can be determined e.g. by applying a mix of antibodies (e.g. "AE1/AE3/PCK26") that selectively stain one or more cytokeratin types. The profiles can be used by anatomic pathologists to detect the presence and/or cell of origin of various tumors.

For example, a cytokeratin profile (data indicating whether a particular set of cytokeratins is expressed in a cell or not) of the cells in the tissue sample can be determined by using fluorescence stains selectively staining the respective cytokeratins. The obtained cytokeratin profile is then compared by the image analysis system against known cytokeratin profiles of various tissues such as liver, lung, colon and so on. In case the cytokeratin profile of a cell in the tissue sample depicted in the image differs from the typical cytokeratin profile of the tissue from which the tissue sample was taken, the cells having this "deviant/untypical" cytokeratin profile are automatically or semi-automatically identified as tumor cells.

According to still other embodiments, the identification of the tumor cells comprises performing an automated analysis of morphological features of the cells (e.g. size, shape, texture, etc) for identifying tumor cells and non-tumor cells. For example, the shape of several tumor cell types differs significantly from their "normally differentiated" counterparts having the same tissue or cell type. The morphological image analysis approach used may depend on the type of tumor cells and the tissue context.

The at least one image may comprise a plurality of monochrome images whose respective pixel intensity values correspond to and indicate the expression level of a particular biomarker having been stained with e.g. a fluorescent or bright field stain and having been photographed via a fluorescent or bright field microscope. The biomarkers may comprise the FAP protein that is selectively expressed in cancer-associated fibroblasts and may comprise tumor-specific biomarkers such as a specific set of cytokeratins or cell proliferation markers. The plurality of images may be generated by applying a color deconvolution algorithm on a multispectral image or by capturing individual monochromatic digital images for each biomarker and respective stain.

According to other embodiments, the at least one digital image comprises an image whose pixel intensity values are indicative of the presence of the FAP protein. The FAP protein is selectively expressed or over-expressed in fibroblasts which are cancer-associated fibroblasts. The identification of the FAP+ areas comprises identifying pixel blobs being local intensity maxima within said digital image.

The identification of the FAP+ areas may comprise applying a predefined and/or heuristically determined intensity threshold or by applying a machine-learning based segmentation algorithm in order to identify FAP+ areas in said digital image for identifying image regions whose pixel intensity values correlate with the intensity of the staining of the FAP in the tissue sample. Said image regions, also referred to as pixel blobs, are used as the FAP+ areas. According to one example, a group of pathologists was asked to modify the intensity threshold until the size and shape of the identified, intensity-dependent FAP+ areas, reproduced the size and shape of typical cancer-associated fibroblasts. The corresponding threshold was stored and used for identifying FAP+ areas when performing an image analysis on other tumor tissue sample images. For example, the intensity threshold can be stored in association with other parameters of the image (e.g. overall brightness, contrast, etc.) and selectively be re-used in a later image analysis step if the other parameters of said later analyzed image are similar to the intensity threshold associated parameter values.

According to other examples, gray scale and color segmentation techniques, edge detection, voting and radial symmetry based image analysis techniques can be used for identifying FAP+ areas. Moreover, various machine learning techniques with supervised learning methods such as SVM (Support vector Machines), DNN (Deep Neural Networks), Random Forest, etc. can be used to identify FAP+ regions and optionally also non-tumor tissue regions and glass regions on a slide.

According to some embodiments, the computation of the proximity measure comprises:
   computing a fraction of the number of the tumor cells whose nearest FAP+ area is less than a predefined distance away from said tumor cell relative to the totality of identified tumor cells; and
   using the fraction as the proximity measure, wherein the higher the fraction, the higher the probability that the classification result indicates that the tumor can effectively be treated by the drug.

Using the totality of measured distances as the proximity measure may be advantageous as the distances can be input directly into the classifier. This algorithm is computationally cheap and particularly suited for mass scans of multiple images provided by a slide scanning device.

According to embodiments, the classification result indicates that the tumor can effectively be treated by the drug selectively in case the fraction of the number of the tumor cells whose nearest FAP+ area is less than the predefined distance away from said tumor cell relative to the totality of identified tumor cells is larger than 90%.

In other words, the tumor is classified as "treatable" by the drug in case $$\frac{\text{number of the tumor cells whose distance to nearest } FAP+ \text{ area} < \text{predef.dist}}{\text{total number of identified tumor cells in digital image or image } FOV \text{ considered}} > 90\%.$$

For example, the classifier can be a rule-based classifier that counts the number of distances being shorter than a predefined threshold and then automatically determining if for more than 90% of the tumor cells a distance was measured that is shorter than said threshold. Again, determining the fraction of the tumor cells having a FAP+ area in their near neighborhood based on comparing the distances with a predefined threshold is computationally cheap and can be executed quickly.

According to other embodiments, the computation of the proximity measure comprises:
  generating a histogram of the number of the identified tumor cells observed in each of at least three distance bins, the histogram covering a distance range of 0 µm to at least 100 µm, each of the bins corresponding to a bar of the histogram, each of the bars indicating a count of the identified tumor cells having a distance to their nearest FAP+ area that falls into said bin;
  connecting the upper end of the first one of the bars with the upper end of the last one of the bars with a straight or curved line, the first bar corresponding to the one of the bins covering the smallest distances, the last bar corresponding to the one of the bins covering the largest distances of the distance range;
  determining the slope of the line; and
  using the slope as the proximity measure.

Computing a histogram may be advantageous as it provides a more detailed picture of the tumor cell—FAP+ distance distribution of a tumor that may be displayed to the user. Thus, the user, e.g. a pathologist or oncologist may use this information to get a better understanding of the microenvironment of a tumor. Different bin width may be used. A typical bin width would represent 10 µm.

According to embodiments, the classification result indicates that the tumor can effectively be treated by the drug selectively in case the slope indicates that more than 90% of the tumor cells are within a predefined distance from their respectively nearest FAP+ area. For example, the classifier may comprise some heuristic rules which evaluate the slope for determining if at least 90% of the distances computed for each of the identified tumor cells are within the predefined distance.

According to embodiments, the predefined distance is in the range of 40 µm to 60 µm, in particular in the range of 45 µm to 55 µm. Preferably, the predefined distance is 50 µm.

It has been observed that this particular distance is a very good threshold criterion for discriminating tumor cells having a "nearby FAP+ area" and those that do not have a "nearby FAP+ area". This distinction has been found to provide a particular high accuracy for predicting if the drug will be able to induce tumor regression or not.

According to embodiments, the identification of the distances comprises identifying, for each of the identified tumor cells, the distance between said tumor cell to the nearest pixel within the one of the identified FAP+ area lying closest to said tumor cell.

According to embodiments, the drug is a bispecific antibody binding to the FAP protein of the cancer-associated fibroblasts and to a further protein expressed on the tumor cells, the binding of the antibody to the further protein promoting tumor regression. The drug can be a "BiTE-antibody", i.e., a bi-specific T-cell engaging antibody.

According to one embodiment, the drug is RG7386 (Peter Brünker et al. in Mol Cancer Ther, 15(5), 946-57, 2016 AACR), a FAP-DR5 antibody that effectively triggers FAP-dependent, avidity-driven DR5 hyperclustering and tumor cell apoptosis.

"Hyperclustering" as used herein refers to the formation of receptor aggregates with an arbitrary number of receptor molecules (as opposed to the formation of dimers or tetramers as several other receptors do). Thus, the number of aggregated receptors may mainly depend on the current local environment and is not limited to a fixed number of predefined binding sites.

According to embodiments, the further protein is a protein triggering apoptosis of the tumor cell.

According to embodiments, the further protein is DR5—"death receptor 5" or DR4—"death receptor 4".

According to embodiments, selectively in case the classification result indicates that the tumor can effectively be treated by the drug, the image analysis system outputs a signal that is indicative of a treatment recommendation to prescribe or apply the drug for treating the tumor.

In a further aspect, the invention relates to an image analysis system for tumor classification. The system is configured for:
  receiving at least one digital image of a tissue sample of a patient;
  analyzing the at least one received image for identifying tumor cells in a region of the at least one received image; the region may be the whole image or a field of view within the image;
  analyzing the at least one received image for identifying FAP+ areas in said region, each FAP+ area being a pixel blob representing one or more cells expressing the fibroblast activation protein—"FAP";
  analyzing the at least one received image for identifying distances between the identified tumor cells and their respective nearest FAP+ area;
  computing a proximity measure as a function of the identified distances;
  processing the proximity measure by a classifier for generating a classification result, the classification result indicating if the tumor of the patient can effectively be treated by a drug or drug-component that binds to the FAP protein; and
  outputting the classification result.

In a further aspect, the invention relates to a method for training a tumor classifier. The method comprises:

receiving, by an image analysis system, a plurality of first digital images respectively depicting a tissue sample of a first cohort of patients having a tumor known to be treatable by a drug, the drug being or comprising a substance that binds to FAP;

receiving, by the image analysis system, a plurality of second digital images respectively depicting a tissue sample of a second cohort of patients having a tumor known to be untreatable by said drug;

for each of the received first digital images, performing, by the image analysis system:

analyzing the first digital image for identifying first tumor cells in a region of said first image;

analyzing said first image for identifying first FAP+ areas in said region, each first FAP+ area being a pixel blob representing one or more fibroblast expressing FAP analyzing said first image for identifying first distances between the identified first tumor cells and their respective nearest FAP+ area;

computing a first proximity measure as a function of the identified first distances;

for each of the received second digital images, performing, by the image analysis system:

analyzing the second digital image for identifying second tumor cells in a region of said second image;

analyzing said second image for identifying second FAP+ areas in said region, each second FAP+ area being a pixel blob representing one or more fibroblast expressing FAP;

analyzing said second image for identifying second distances between the identified second tumor cells and their respective nearest FAP+ area;

computing a second proximity measure as a function of the identified second distances;

processing the first proximity measures in association with a "treatable" class membership tag and processing the second proximity measures in association with an "untreatable" class membership tag by an untrained classifier for generating a trained classifier. The trained classifier is configured to indicate, upon receiving a proximity measure for a slide of a further patient as input, if the tumor of the further patient can effectively be treated by a drug or drug-component that binds to FAP. For example, the classifier that generates the classification result indicating if the tumor of the patient can effectively be treated by a drug or drug-component that binds to the FAP protein that is described herein for various embodiments of the invention can be generated by the above described training method.

For example, the classifier may be a rule-based classifier comprising a rule R: "if the fraction of tumor cells lying within a predefined distance PD1 from the respective nearest FAP+ area exceeds a predefined fraction F1 of all identified tumor cells, output a prediction that the drug will be effective in treating the tumor; otherwise, the drug will not be effective". The combination of parameters PD1 and F1 which generate a tumor cell classification that has the smallest deviation ("error") from the training data set is used by the trained classifier in any further classification step for determining the fraction of tumor cells having at least one "nearby" FAP+ area. For a training data set consisting of multiple colon cancer tissue sample images of two cohorts of patients (treatable and untreatable by a particular FAP binding drug) a good classification result was obtained for the parameter values F1=90% and the predefined distance PD1 being 50 μm.

The above training method can be used for generating the classifier that predicts whether a drug will be effective in treating the tumor of a patient or not and that is described herein for embodiments of the invention.

According to embodiments, the classification result are displayed by representing all identified tumor cells whose distance to the respective nearest FAP+ area is below the predefined distance in a different color than those tumor cells whose distance is above said predefined distance. The two different colors may be presented as an overlay of the digital image of the tumor tissue sample of the patient (e.g. a bright field image). Thus, a user, e.g. a pathologist, will be able to intuitively grasp the fraction of tumor cells that are treatable by a drug directed at the FAP+ protein within all identified tumor cells. The user can immediately and easily derive from such an overlay image whether the treatment of the patient with the drug will be effective in treating this tumor or not.

For example, the tissue sample may be a biopsy sample of colorectal cancer. However, the method and system according to embodiments of the invention are also applicable to other cancer types, e.g. breast cancer, pancreatic cancer, lung cancer, etc.

The at least one image may be a bright field image wherein tumor cells are colorized with blue color and/or wherein pixels being indicative of the presence of the FAP protein are shown in brownish color, e.g. based on a DAB staining.

The tissue sample can be a whole slide tissue sample and the digital image can be a whole slide image. Typically, such whole slide tissue samples comprise several thousand or even 10,000s of cells. Thus, the proximity measure may be a function of the distances of many thousand neighboring FAP+ area-tumor cell pairs.

BRIEF DESCRIPTION OF THE DRAWINGS

In the following embodiments of the invention are explained in greater detail, by way of example only, making reference to the drawings in which.

DETAILED DESCRIPTION

Figure 1:
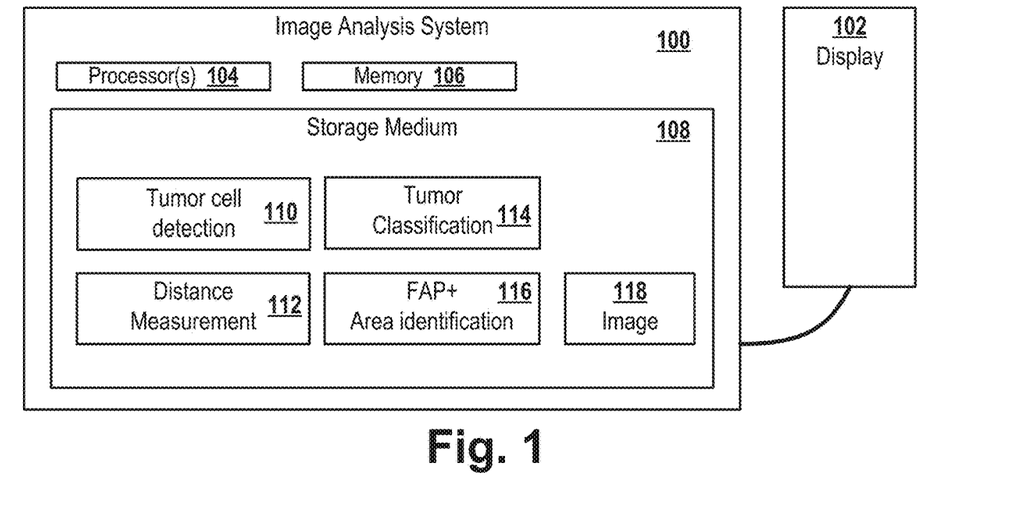
FIG. 1 is a block diagram of an image analysis system.

FIG. 1 is a block diagram of an image analysis system 100 according to an embodiment of the invention. The system comprises one or more processors 104, a main memory 106 and a non-volatile storage medium 108. The storage medium comprises one or more application programs or modules 110, 114, 112, 116 configured for performing one or more image processing tasks. For example, a first module 110 may perform a connected component analysis and edge detection routines in order to identify pixel blobs representing cells, in particular tumor cells. The identification may be performed by analyzing one or more monochromatic fluorescent or brightfield microscopy images having been derived from the same tissue sample whereby the pixel intensities of the different monochromatic images respectively are indicative of a particular biomarker or a particular set of biomarkers. For example, a specific set of cytokeratins may be stained with suitable antibodies which are coupled to a fluorescent or colored dye. Multiple monochromatic images 118 can be derived from a multi-spectral fluorescent image of a particular tissue sample by applying a color deconvolution algorithm.

For example, primary antibody Anti-Pan Keratin "AE1/AE3/PCK26" of Ventana Medical Systems, Inc. can be used to stain poorly differentiated malignant tumors. A set of anti-Pan Keratin antibodies "AE1/AE3/PCK26" specifically binds to antigens located in the cytoplasm of simple and complex epithelial cells. It is a mouse monoclonal antibody cocktail raised against an epitope found on human epidermal keratins as reported by Woodcock-Mitchell, et al. This antibody cocktail reacts with the 56.5 kD, 50 kD, 50' kD, 48 kD, and 40 kD cytokeratins of the acidic subfamily and 65-67 kD, 64 kD, 59 kD, 58 kD, 56 kD, and 52 kD cytokeratins of the basic subfamily.

AE1/AE3 und PCK26 are the clones of the cells producing the antibody cocktail. The antibodies of each of the clones detect a specific subset of Keratins:

PCK26 specifically binds to Keratins of type II: KRT5, KRT6, KRT8. The antibodies react with keratins of the following species: human, mouse, sheep, pig.

AE1 specifically binds to Keratins of type I: KRT10, KRT14, KRT15, KRT16, KRT19. The antibodies react with keratins of the following species: human and rat.

AE3 specifically binds to Keratins of type II: KRT1, 2, 3, 4, 5, 6, 7, 8. The antibodies react with keratins of the following species: human, rat and mouse.

The storage medium 108 may comprise the one or more digital images 118. For example, the digital images may be stored in the storage medium 108 after their generation by a color deconvolution algorithm or after their acquisition by a camera or other capturing device. Moreover, the system 100 is coupled to or comprises a display 102, e.g. an LCD display. The system uses the display 102 for displaying the digital images 118 of tissue samples of various patients, for displaying a bright field image where tumor cells and FAP+ stroma cells are stained with different dyes and are shown in different colors, for displaying distances measured by the distance measurement module 112 in the form of one or more histograms and/or for displaying a tumor classification result or treatment suggestion generated by the classifier module 114.

For example, a tissue sample, e.g. a colon cancer biopsy sample, is used that has been stained by a plurality of biomarker specific stains. Pan Cytokeratin [AE1/AE3] of BioCare medical, a concentrated and prediluted antibody cocktail (Control Number: 901-011-013015) can be used for identifying cells which express a specific set of cytokeratins and which are identified as tumor cells. Pan Cytokeratin [AE1/AE3] is a mouse monoclonal antibody cocktail that is intended for laboratory use in the qualitative identification of a broad spectrum of acidic and basic cytokeratin proteins by immunohistochemistry (IHC) in formalin-fixed paraffin-embedded human tissues. Intensity signals of said stain(s) and the corresponding monochromatic images are analyzed by module 110 for identifying tumor cells.

In addition, a further stain that selectively stains the FAP protein which is selectively expressed in cancer-associated fibroblasts is used for staining the tissue sample. For example, a FAP antibody that is directly or—via secondary antibodies or other conjugating agents—coupled to a particular dye is used in a staining protocol to selectively stain cells expressing the FAP protein. The dye may be a fluorescent or bright field image dye. For example, the dye may be diaminobenzidine (DAB) that causes FAP+ cells to appear as brownish regions in a bright field microscope as depicted e.g. in FIG. 6. In addition, counterstains, e.g. H&E staining, may be used for staining other cells and nuclei and ease the discrimination of tissue regions and non-tissue regions in the image. Alternatively, a fluorescent stain that selectively binds to FAP may be used. In case the image that comprises the signal of the FAP-specific stain is a multichromatic image, a color deconvolution is applied for generating a monochromatic image whose pixel intensity values selectively represent the signal generated by said FAP-specific stain.

Intensity signals of said FAP-specific stains are analyzed by module 116 for identifying FAP+ areas, i.e. pixel areas which are indicative of the presence of the FAP protein in a cell. A FAP+ area can have circular or oval shape and can represent a single FAP+ fibroblast. Likewise, a FAP+ area can have any other shape and size and may represent a plurality of adjacent and/or partially overlapping FAP+ fibroblasts. According to some example embodiments, the FAP+ areas can be identified by applying an intensity threshold on pixel intensities for identifying local intensity maxima in the monochromatic digital image whose pixel intensity values correlate with the staining intensity of the FAP-specific stain.

After having identified tumor cells and FAP+ areas in the one or more digital images of a particular tissue slide of a patient, the distance of each of the identified tumor cells and its respective nearest FAP+ area is measured by module 112. For example, module 112 identifies the center of each tumor cell and determines the distance to the nearest pixel within the one of the FAP+ areas that is closest to said tumor cell. Alternatively, module 112 identifies, for each of the identified tumor cells, the shortest distance between any pixel within said tumor cell and the nearest pixel within the one of the FAP+ areas that is closest to said tumor cell.

In some embodiments, the tumor cells, FAP+ areas and their respective nearest distances are computed for whole slide images. Alternatively, the user or a program module may select a sub-region within a whole slide image and the tumor cell identification, the FAP+ area detection and the distance determination is performed selectively for the selected sub-region. The sub-region is also referred to as "field of interest" (FOV).

The distances measured by module 112 are processed by the application program or module 114 which computes a proximity measure as a function of the distances. For example, the module 114 computes a fraction of tumor cells lying within a predefined distance threshold away from the next FAP+ area and the totality of identified tumor cells. In addition or alternatively, histograms as depicted e.g. in FIGS. 3 and 4 may be computed by the module 114. The histograms may be displayed on the display 102 to provide a pathologist a graphical representation of the distribution of the measured distances. In addition or alternatively, the slope of a linear or curved line connecting the top borders of the individual bars of a histogram may be determined for assessing the distribution of the distances between tumor cells and their nearest FAP+ areas in an image. This information has been observed to be a good predictor for the question whether a particular tumor can be treated with a drug that binds to the FAP protein.

In addition, the classifier 114 or another module may use the distance information for generating an overlay image wherein tumor cells lying within the predefined distance from its nearest FAP+ area are overlaid or represented by a different color than tumor cells lying farther away from their nearest FAP+ area than the predefined distance.

According to preferred embodiments, the "predefined distance", also referred to as "predefined distance threshold", is the physiologically effective distance" of the drug to be used. Thus, this predefined distance indicates the maximum distance between a drug having bound to a FAP protein and a tumor cell where a causative effect of the drug on the tumor cell can be observed, e.g. in in-vitro studies, in animal tests or in clinical trials.

Figure 2:
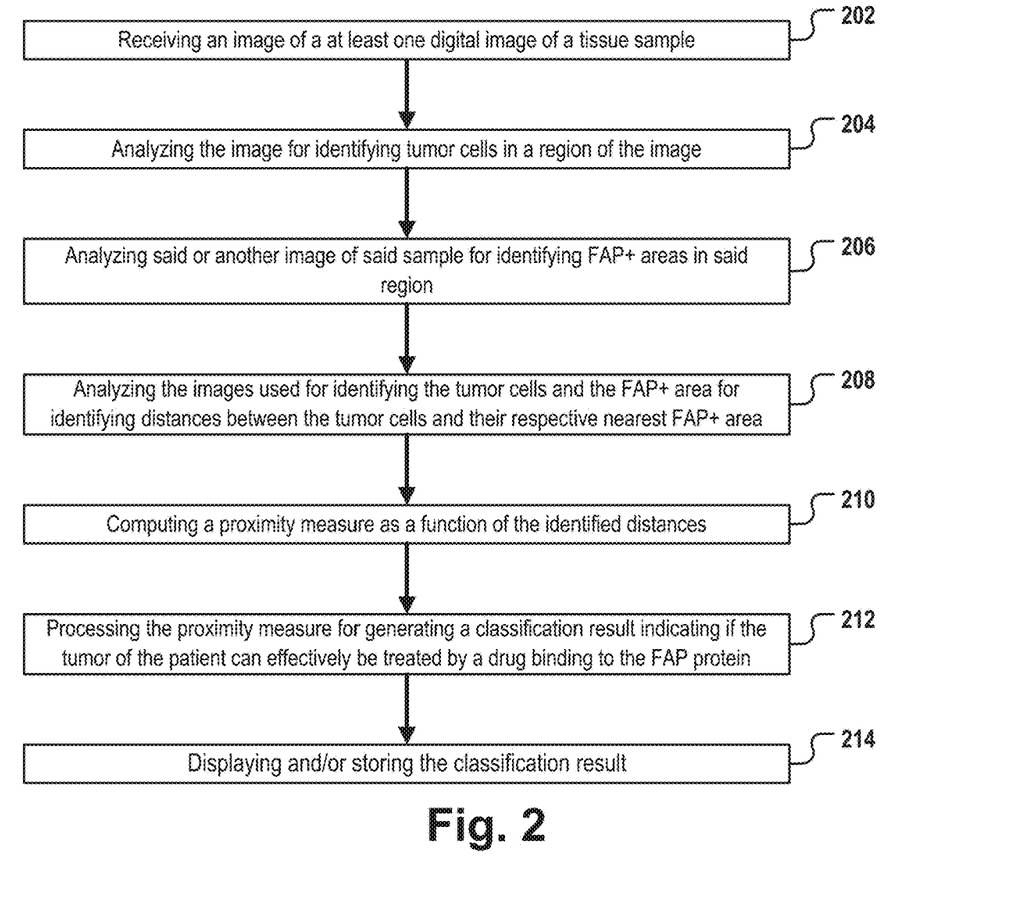
FIG. 2 is a flow chart of an image analysis method for classifying tumors.

FIG. 2 is a flow chart of an image analysis method for classifying tumors. The methods depicted in FIG. 2 can be implemented, for example, by an image analysis system 100 as depicted in FIG. 1.

In a first step 202, the image analysis system receives one or more digital images 118 of a tissue sample. The one or more digital images can be a multispectral fluorescent immunohistochemistry (IHC) image that is decomposed by the image analysis system into a plurality of monochromatic images by applying a color deconvolution algorithm. Alternatively, the image analysis system may receive a plurality of monochromatic digital images of the tissue sample. The multispectral digital image and/or the plurality of monochromatic digital images of the tissue sample can be provided via an interface with an image acquisition system (e.g. a microscope or slide scanning device). Alternatively, the image analysis system 100 may receive the digital images of the tissue sample by reading the images from a storage medium, e.g. a CD-ROM or flash drive.

For example, the tissue sample from which the images where derived can be a biopsy of a colorectal cancer tissue sample. The sample has been stained with one or more stains selectively binding to a set of cytokeratins and with a further stain that selectively binds to the FAP protein. Pixel regions representing local intensity maxima of the cytokeratin signal (CK+ signal) are identified as tumor cells. Pixel regions representing local intensity maxima of the FAP signal are identified as FAP+ areas. A "FAP signal" as used herein is a light signal emitted by a stain that selectively stains the FAP protein, whereby said light signal is represented in the form of pixel intensity values in a respective monochromatic image that selectively captures the emission spectrum of the stain used for selectively staining the FAP protein. This definition applies analogously also to the other "biomarker signals".

According to one example implementation, digital images of IHC-stained glass slides were acquired with a Ventana iScan HT Slide Scanner. Images were viewed and organized using the Roche IRIS Platform. Ventana image analysis software VDP-SKD and the Ventana Digital Pathology Software Development Kit was used for performing most of the image analysis methods for identifying the cell boundaries and for identifying separate tissue and glass regions, tumor cells and FAP+ areas.

In a second step 204, module 110 of the image analysis system performs one or more image analysis routines for identifying tumor cells and optionally also further cell types and/or other morphological structures in the received digital image or images of the tissue sample. Image analysis routines for detecting cells which are known in the art may be used, e.g. cell detection methods being based on a connected component analysis, gray scale and color segmentation techniques, intensity thresholding and the like.

In a further step 206, module 116 performs one or more image analysis routines for identifying FAP+ areas in the received digital image or images of the tissue sample.

For example, threshold based image analysis routines for identifying local intensity maxima in a monochromatic image that selectively comprises FAP+ signals may be performed for detecting the FAP+ areas. In addition or alternatively to the threshold, a connected component analysis, gray scale and color segmentation techniques and the like are used for identifying FAP+ areas.

In a further step 208, module 112 of the image analysis system determines, for each of the identified tumor cells, the distance of the tumor cell to the nearest FAP+ area, e.g. by measuring the distance between a first and a second pixel, the first pixel being a pixel within an identified tumor cell lying closest to the nearest FAP+ area of said tumor cell, the second pixel being a pixel within said FAP+ area lying closest to said identified tumor cell.

Figure 6:
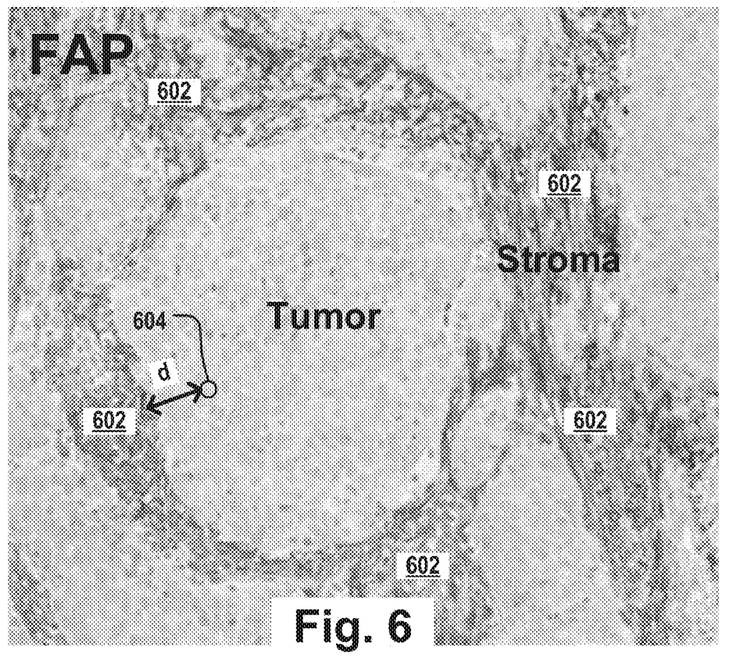
FIG. 6 is a bright field image of a tumor tissue slide comprising tumor cells and FAP+ areas.

Some FAP+ areas are depicted in FIG. 6 as dark grey (DAP-stained) image regions 602 and one of the identified tumor cells is depicted in FIG. 6 as a circle 604. The distance d is the distance that was measured by module 112 between the tumor cell 604 and its nearest FAP+ area 602.

After step 208 has completed, module 114 computes in step 210 a proximity measure as a function of the determined distances. For example, the proximity measure can be a fraction of tumor cells having at least one "near FAP+ area" within a predefined distance and the totality of tumor cells identified in said image of image FOV. This fraction describes the fraction of tumor cells that can potentially be attacked by a drug that binds to the FAP+ protein.

In addition, or alternatively a slope of two or more bins of a distance histogram can be computed as the proximity measure.

According to one embodiment, a negative slope (from short distance bins to long distance bins) indicates that the majority of tumor cells can potentially be attacked by a drug that binds to the FAP protein and a positive slope (from short distance bins to long distance bins) indicates that the majority of tumor cells can probably not be attacked successfully by a drug that binds to the FAP protein. Thus, in case of a negative slope, the tumor cells will be classified as "treatable" by the drug, and in case of a positive slope, the tumor cells will be classified as likely "not being treatable" by the drug. According to other embodiments, which may be particularly advantageous for some types of tumors or drugs, the rate of the descent of the slope may be used as the predictor for drug effectiveness: if the rate of the descent of the slope exceeds a predefined threshold, the tumor cells will be classified as "treatable" by the drug, and in case of a negative slope whose rate of descent is below the predefined threshold, the tumor cells will be classified as likely "not being treatable" by the drug.

Thus, according to some embodiments, the classification result indicates that the tumor can effectively be treated by the drug selectively in case the slope is negative. In other embodiments, the classification result indicates that the tumor can effectively be treated by the drug selectively in case the rate of decrease of the slope exceeds a predefined threshold value.

In step 212, module 114 classifies the identified tumor cells into tumor cells that are (probably) treatable by the disease that binds to the FAP protein and in tumor cells that are (probably) untreatable by said drug. For example, if the fraction of tumor cells lying not more than 50 µm away from the respective nearest FAP+ area is 90% or higher, and/or if the slope is negative (e.g. has a negative slope exceeding a predefined threshold), the tumor cells are classified as treatable tumor cells. If the fraction of tumor cells lying not more than 50 µm away from the respective nearest FAP+ area is below 90% and/or if the slope is positive or the slope is negative but does not exceed the above mentioned slope threshold, the tumor cells are classified as untreatable tumor cells (untreatably by the particular drug).

Given the complexity of cancer-related changes in the metabolism and signaling pathways of cells, the concept of "treatability" of a cancer by a particular drug as used herein also covers the situation that a drug might not be able to cure a patient from cancer but at least has been shown to increase the disease free survival time, to slow down cancer progression, to improve the overall state of health, to increase the chances of a treatment success by applying another drug or at least to increase the likelihood of any one of said effects.

Accordingly, the concept of "untreatability" of a cancer by a particular drug as used herein also covers the situation that a drug has been shown not to increase the disease free survival time, not to slow down cancer progression, not to improve the overall state of health, not to increase the chances of a treatment success by applying another drug or not to increase the likelihood of any one of said desired effects.

In step 214, the image analysis system 100 outputs the classification result. For example, the prediction whether or not the tumor is treatable by the drug and/or the proximity measure and any histograms or other plots are stored in a storage medium 108. In addition, or alternatively, said classification results and/or histograms and plots are displayed on a display device 102. For example, the computed fraction and the histograms depicted in FIGS. 3, 4 and 5 and the digital image with the identified tumor cells and FAP+ areas can be displayed on an LCD display 102 coupled to the image analysis system 100.

Figure 3A:
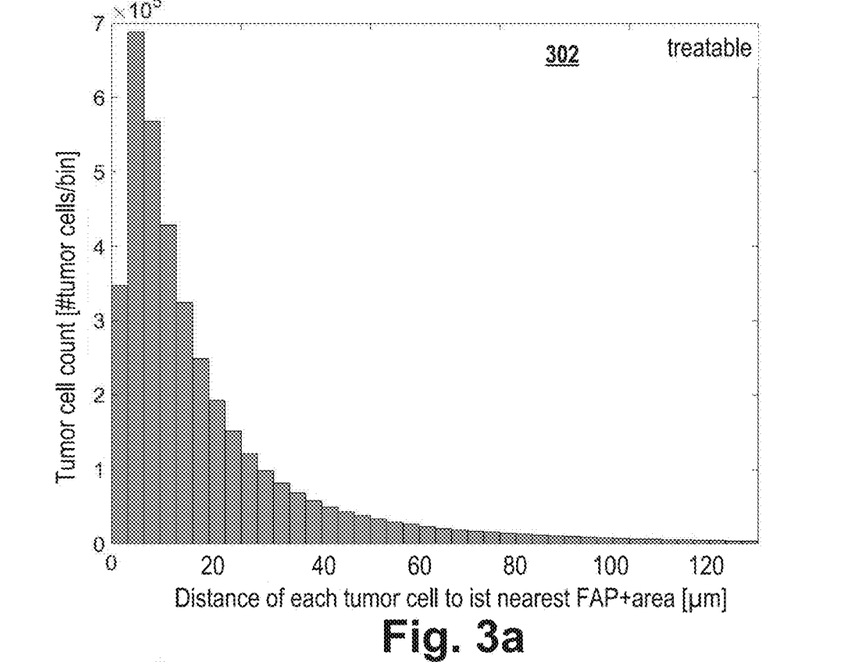
FIGS. 3a, b depict histograms of the distances obtained from tissue slide images of a treatable and an untreatable patient cohort.

FIG. 3a depicts a histogram 302 of the measured distances between each of the identified tumor cells to their respective nearest FAP+ area. The distances were obtained from a colon cancer tissue slide image of a patient whose tumors are known to be treatable by a drug that binds to the FAP+ protein.

Figure 3B:
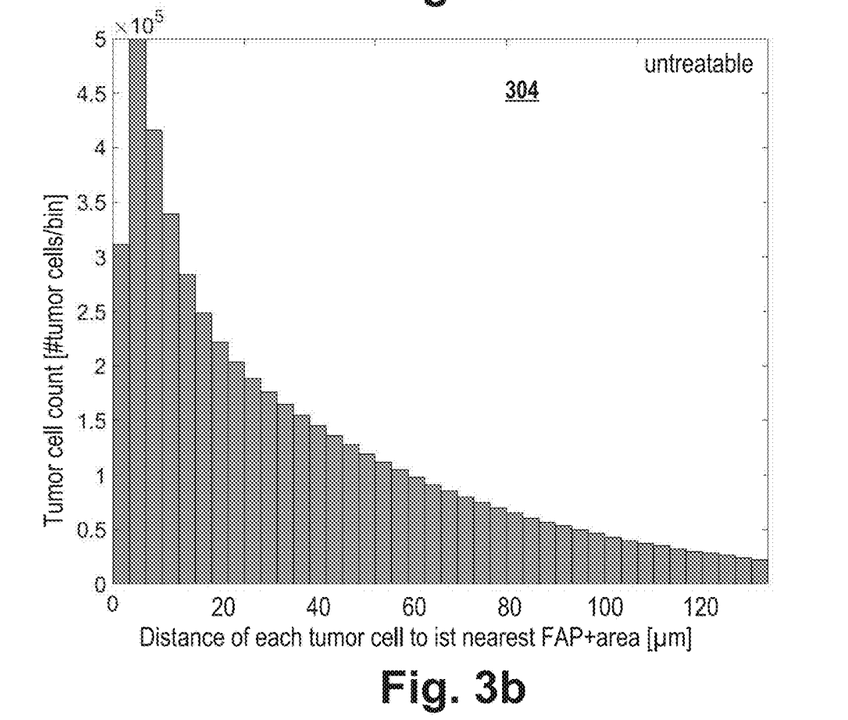

FIG. 3b depicts a histogram 304 of the same type of measured distances. The distances were obtained from a colon cancer tissue slide image of a patient whose tumors are known to be untreatable by a drug that binds to the FAP+ protein. As can be derived from FIGS. 3a and 3b, the fraction of tumor cells lying in close spatial proximity to at least one FAP+ area is significantly larger for in the "treatable" patient than in the "untreatable" patient.

Figure 3C:
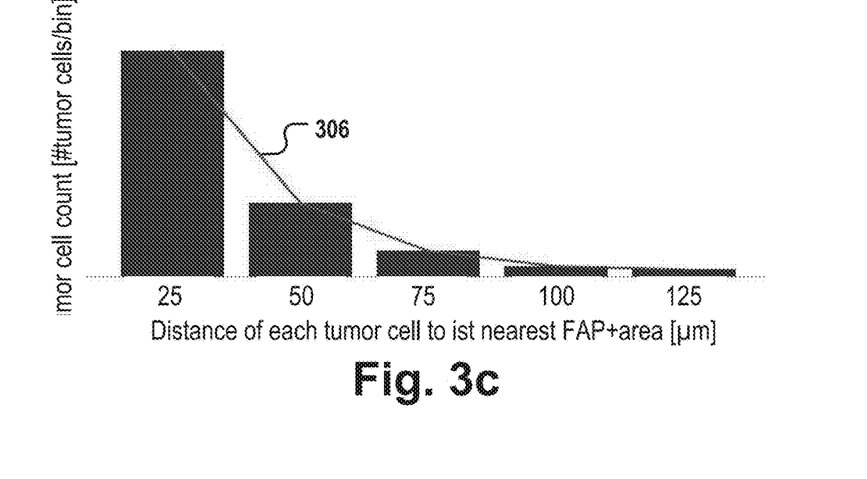
FIG. 3c depicts how a slope of a histogram can be computed.

FIG. 3c illustrates how a slope can be derived from a histogram of distances: the histogram comprises five distance bins. The first been covers a distance of 0 µm to 25 µm, the second been covers a distance from 26 µm to 50 µm, the third been covers a distance of 51 µm to 75 µm and so on. The term "distance" relates to the distance of anyone of the identified tumor cells to its nearest identified FAP+ area. The image analysis system uses information on the resolution and/or zoom factor of the image as input for computing the tumor cell-FAP+ area distance in µm from the numbers of pixels separating e.g. the boundaries of the tumor cell and the FAP+ area within one image. For each bin, a corresponding bar is plotted in the histogram, whereby the height of each bar reflects the number of tumor cells whose distance to its nearest FAP+ area falls within said bin.

The slope of the histogram can be computed to provide a proximity measure for the tumor cells that is used by a classifier for classifying the tumor. By plotting a straight or curved line that connects the top of the bar of the first bin with the top of the bar of the last bin and by determining the slope of that line, a negative (falling) slope will be identified. A negative slope in the distance histogram whose absolute amount exceeds a slope minimum value is used as a proximity measure that indicates whether the tumor cells of the tumor are treatable by a particular drug. As can be inferred from FIGS. 3a-3c, the shape of the histogram bars and the slope of the connecting line 306 are indicative of the fraction of tumor cells having a "nearby" FAP+ area.

Figure 4:
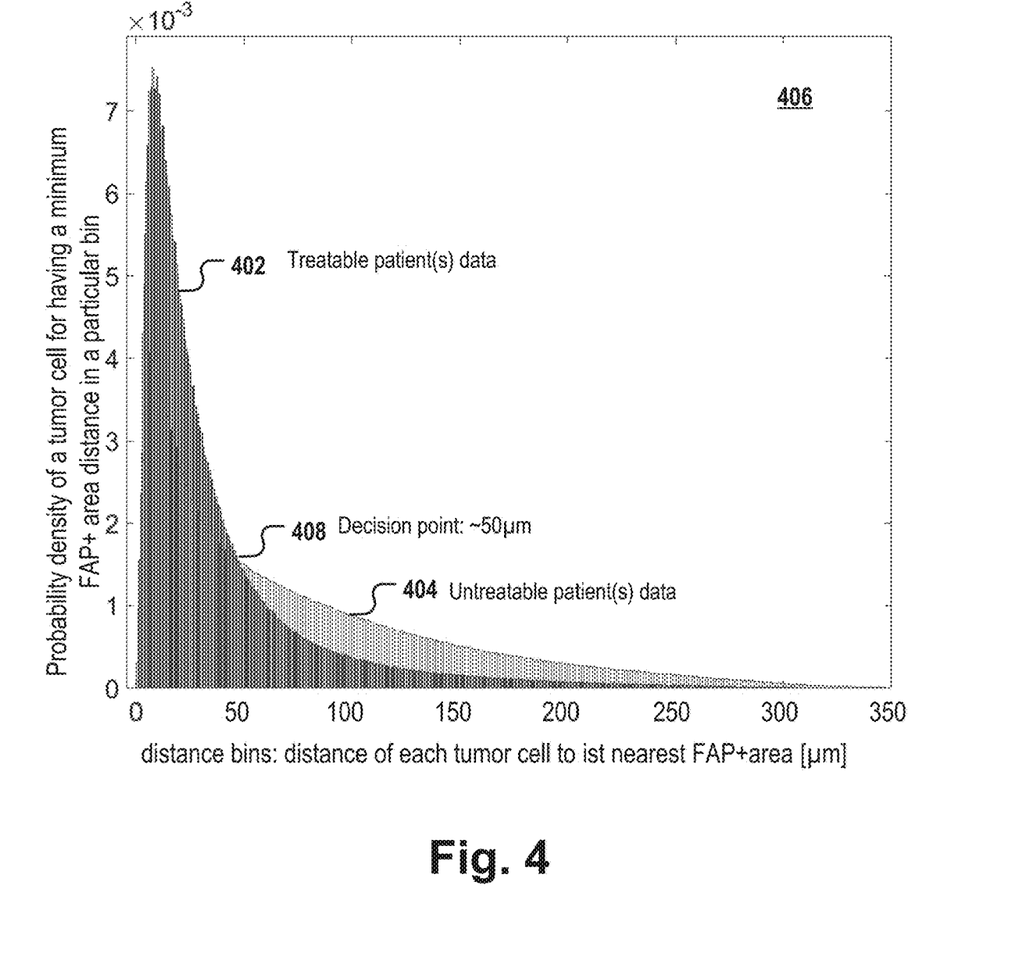
FIG. 4 depicts a histogram comprising an overlay of the distances obtained from tissue slide images of a further treatable and a further untreatable patient cohort.

FIG. 4 is a combined plot 406 of a first 402 and a second 404 probability density function respectively having the form of a histogram.

A probability density function (PDF) is a function that describes the relative likelihood for a variable to take on a given value. The probability of the variable falling within a particular range of values is given by the integral of this variable's density over that range—that is, it is given by the area under the density function but above the horizontal axis and between the lowest and greatest values of the range. The probability density function is nonnegative everywhere, and its integral over the entire space is equal to one.

Each probability density function and respective histogram indicates the probability that for a particular tumor cell, the measured minimum distances to its respective nearest FAP+ area is within a particular distance bin. The probabilities represented by the first histogram 402 were obtained from a colon cancer tissue slide image of a further patient whose tumors are known to be treatable by a drug that binds to the FAP+ protein. The probabilities represented by the second histogram 404 were obtained from a colon cancer tissue slide image of a still further patient whose tumors are known to be untreatable by said drug.

As can be derived from FIG. 4, the probability functions of the treatable and the untreatable patient differ and correspond to two different distance probability curves which intersect at the decision point 408. In the depicted example, the decision point is about 50 µm. It has been observed that the physiologically effective distance of a FAP-bound drug against the tumor is typically 50 µm. Thus, it has been observed that patients having a tumor whose vast majority of tumor cells is less than 60 µm, more preferentially less than 55 µm and more preferentially less than 50 µm away from said tumor cell's nearest FAP+ area can likely benefit from a treatment that is based on the application of a drug that binds to the FAP+ protein.

The decision point 408, i.e., the point where the two probability density curves 402, 404 intersect, can be used as a rough estimate for the physiologically effective distance threshold that is suitable for classifying the tumor into treatable vs. untreatable in respect to a particular drug. The physiologically effective distance may depend on the drug to be used and the signaling cascades whose activities are modified by the drug. Thus, by determining the distance distributions both for patients known to be treatable by a particular drug and for patients known to be untreatable by said drug, the intersection point of said drug can be derived from a plot as depicted in FIG. 4 and can be used as the distance threshold for classifying the tumor cells into "treatable" vs. "untreatable": if more than a predefined minimum fraction (e.g. 90%) of the tumor cells lie within the "decision point distance", e.g. 50 µm, said tumor is predicted to be treatable by said drug.

Figure 5:
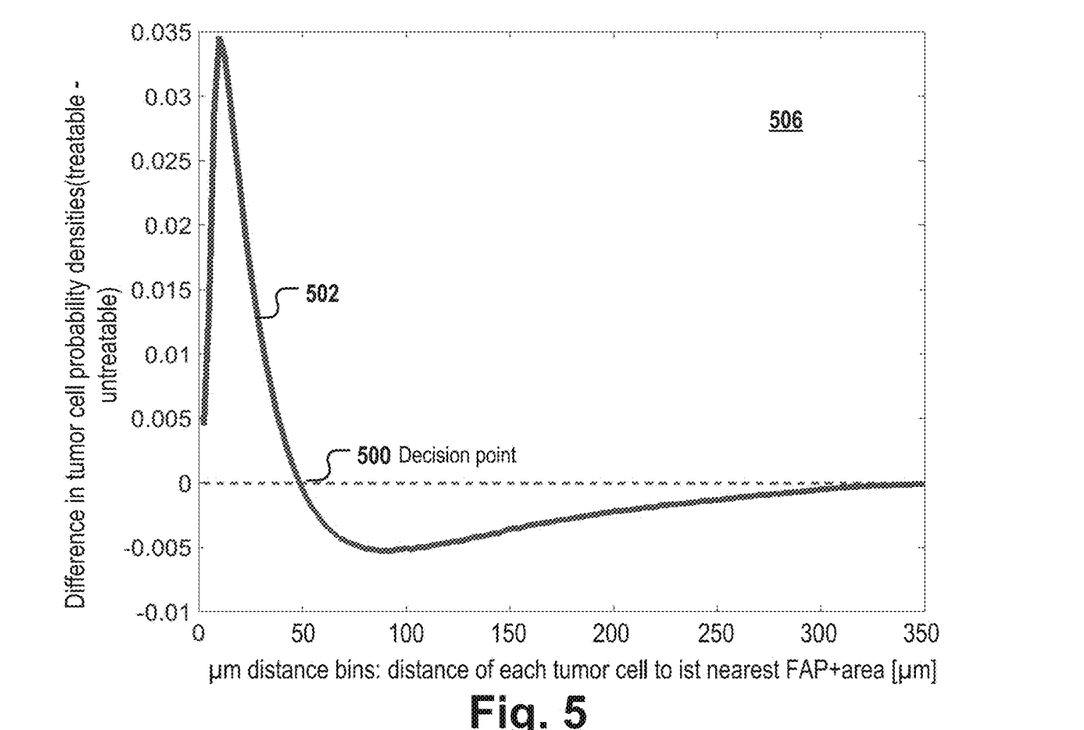
FIG. 5 depicts differences of the distances of the treatable minus untreatable patient cohort depicted in FIG. 4.

FIG. 5 depicts a further plot 506 that is a derivative of the probability functions 402, 404 of plot 406. The y-axis of plot 506 represents the difference between a first and a second probability that a distance obtained for a particular tumor cells is covered by a given distance bin, whereby the first probability is derived from a patient that was treatable by a particular drug and whereby the second probability is derived from a patient that was untreatable by a particular drug. In this plot, the decision point 500 is determined as the point where the difference function 502 crosses the "zero" base line.

FIG. 6 depicts several FAP+ areas as dark grey (DAP-stained, actually brownish) image regions 602. One of the identified tumor cells is depicted as a circle 604. The distance d is the distance that was measured by module 112 between the tumor cell 604 and its nearest FAP+ area 602. In the same way, a distance d is determined for each of the tumor cells identified in the tissue slide image. The automated measurement of minimum tumor cell-FAP+ area distances in a tissue sample on a whole slide level provides a more comprehensive and accurate insight into the tumor biology of a patient.

Figure 7:
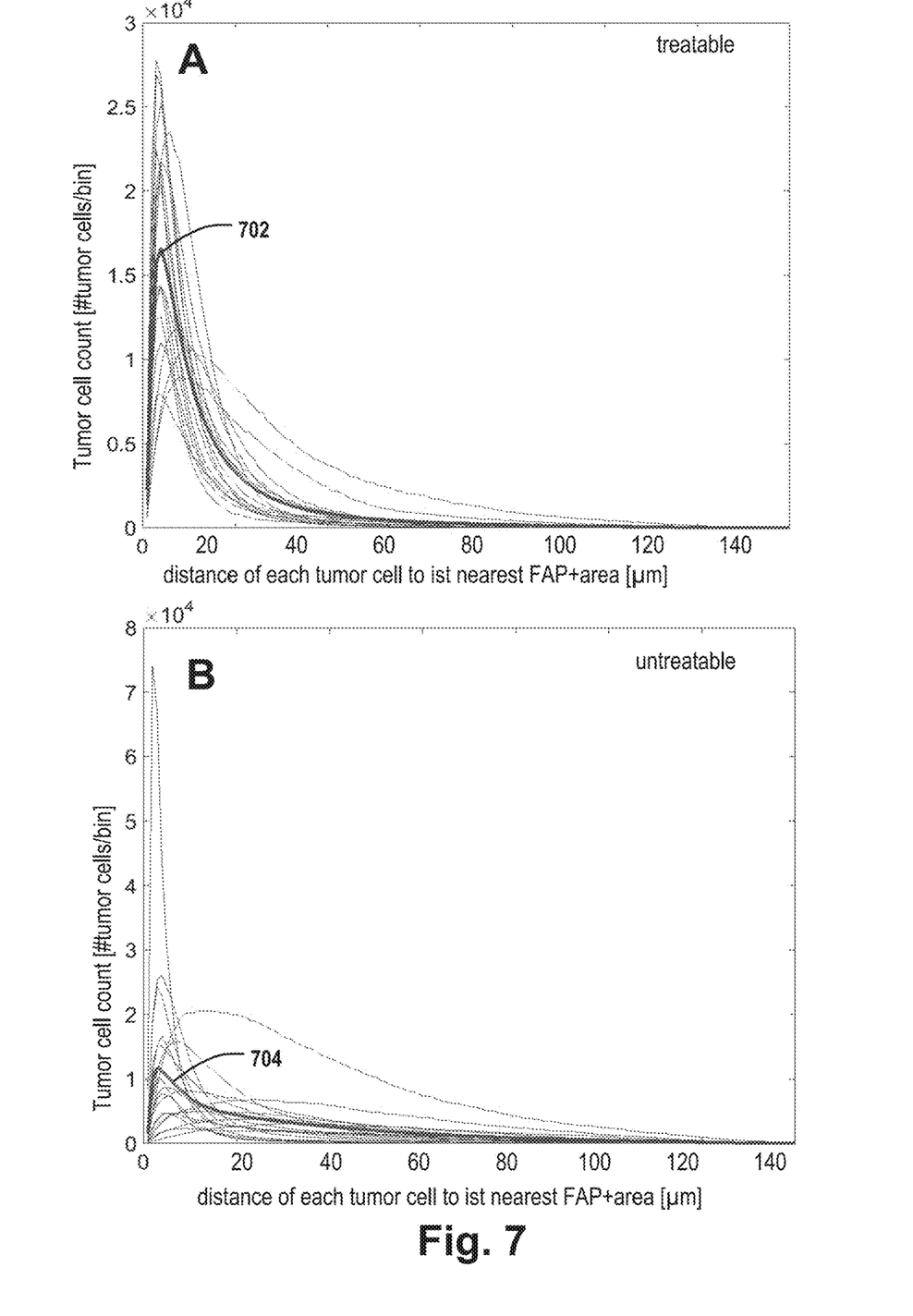
FIG. 7 depicts two plots indicating the probability density that a particular tumor cell lies within a given distance from its nearest FAP+ area for multiple different treatable and untreatable patients.

FIG. 7a depicts, for each of a plurality of colon cancer patients of a first patient cohort, measured distances between each of a plurality of tumor cells identified in a tissue sample image of said patient to their respective nearest FAP+ area. Each curve corresponds to a patient whose tumors are known to be treatable by a drug that binds to the FAP+ protein. The bold curve 702 is the arithmetic mean of all other distance distribution curves depicted in the plot of FIG. 7a.

FIG. 7b depicts, for each of a plurality of colon cancer patients of a second patient cohort, measured distances between each of a plurality of tumor cells identified in a tissue sample image of said patient to their respective nearest FAP+ area. Each curve corresponds to a patient whose tumors are known to be untreatable by a drug that binds to the FAP+ protein. The bold curve 704 is the arithmetic mean of all other distance distribution curves depicted in the plot of FIG. 7b.

The drug that was used for generating the plots in FIGS. 3, 4, 5 and 7 was RG7386, a FAP-DR5 antibody that triggers DR5 hyperclustering and tumor cell apoptosis.

The invention claimed is:

1. An image analysis method for tumor classification, the method comprising:
receiving, by an image analysis system, at least one digital image of a tissue sample of a patient;
analyzing, by the image analysis system, the at least one received image for identifying tumor cells in a region of the at least one received image;
analyzing, by the image analysis system, the at least one received image for identifying FAP+ areas in said region, each FAP+ area being a pixel blob representing one or more cells expressing the fibroblast activation protein —"FAP";
analyzing, by the image analysis system, the at least one received image for identifying distances (d) between the identified tumor cells and their respective nearest FAP+ area;
computing, by the image analysis system, a proximity measure as a function of the identified distances;
processing the proximity measure by a classifier for generating a classification result, the classification result indicating if the tumor of the patient can effectively be treated by a drug or drug-component that binds to the FAP protein; and
outputting, by the image analysis system, the classification result.

2. The image analysis method of claim 1, the tissue sample being a whole slide tissue sample and the digital image being a whole slide image.

3. The image analysis method of claim 1, the identification of the tumor cells comprising:
identifying proliferating non-lymphoid cells (KI67$^+$ CD3$^-$) and using said identified cells as the tumor cells; and/or
identifying cells expressing or over-expressing a set of one or more tumor-specific biomarkers and using said identified cells as the tumor cells.

4. The image analysis method of claim 3, the one or more tumor-specific biomarkers being a cytokeratin or a set of two or more cytokeratins.

5. The image analysis method of claim 1, the at least one digital image comprising an image whose pixel intensity values are indicative of the presence of the FAP protein, the FAP protein being selectively expressed or over-expressed in cancer-associated fibroblasts, the identification of the FAP+ areas comprising identifying pixel blobs being local intensity maxima within said digital image.

6. The image analysis method of claim 1, the computation of the proximity measure comprising:
computing a fraction of the number of the tumor cells whose nearest FAP+ area is less than a predefined distance away from said tumor cell relative to the totality of identified tumor cells; and
using the fraction as the proximity measure, wherein the higher the fraction, the higher the probability that the classification result indicates that the tumor can effectively be treated by the drug.

7. The image analysis method of claim 6, the classification result indicating that the tumor can effectively be treated by the drug selectively in case the fraction of the number of the tumor cells whose nearest FAP+ area is less than the predefined distance away from said tumor cell relative to the totality of identified tumor cells is larger than 90%.

8. The image analysis method of claim 1, the computation of the proximity measure comprising:
generating a histogram of the number of the identified tumor cells observed in each of at least three distance bins, the histogram covering a distance range of 0 µm to at least 100 µm, each of the bins corresponding to a bar of the histogram, each of the bars indicating a count of the identified tumor cells having a distance to their nearest FAP+ area that falls into said bin;
connecting the upper end of the first one of the bars with the upper end of the last one of the bars with a straight or curved line, the first bar corresponding to the one of the bins covering the smallest distances, the last bar corresponding to the one of the bins covering the largest distances of the distance range;
determining the slope of the line; and
using the slope as the proximity measure.

9. The image analysis method of claim 8, the classification result indicating that the tumor can effectively be treated by the drug selectively in case the slope indicates that more than 90% of the tumor cells are within a predefined distance from their respectively nearest FAP+ area.

10. The image analysis method of claim 6, the predefined distance being in the range of 40 µm to 60 µm.

11. The method of any claim 1, the identification of the distances comprising identifying, for each of the identified tumor cells, the distance between said tumor cell to the nearest pixel within the one of the identified FAP+ area lying closest to said tumor cell.

12. The image analysis method of claim 1, the drug being a bispecific antibody binding to the FAP protein of the cancer-associated fibroblasts and to a further protein expressed on the tumor cells, the binding of the antibody to the further protein promoting tumor regression.

13. The method of claim 12, the further protein being a protein triggering apoptosis of the tumor cell, the further protein being DR5—"death receptor 5" or DR4—"death receptor 4".

14. The image analysis method of claim 1, the method further comprising:
    selectively in case the classification result indicates that the tumor can effectively be treated by the drug, outputting a signal being indicative of a treatment recommendation to prescribe or apply the drug for treating the tumor.

15. An image analysis system for tumor classification, the system including one or more processors and a memory configured for:
    receiving at least one digital image of a tissue sample of a patient;
    analyzing the at least one received image for identifying tumor cells in a region of the at least one received image;
    analyzing the at least one received image for identifying FAP+ areas in said region, each FAP+ area being a pixel blob representing one or more cells expressing the fibroblast activation protein—"FAP";
    analyzing the at least one received image for identifying distances between the identified tumor cells and their respective nearest FAP+ area;
    computing a proximity measure as a function of the identified distances;
    processing the proximity measure by a classifier for generating a classification result, the classification result indicating if the tumor of the patient can effectively be treated by a drug or drug-component that binds to the FAP protein; and
    outputting the classification result.

16. A method for training a tumor classifier, the method comprising:
    receiving, by an image analysis system, a plurality of first digital images respectively depicting a tissue sample of a first cohort of patients having a tumor known to be treatable by a drug, the drug being or comprising a substance that binds to FAP;
    receiving, by the image analysis system, a plurality of second digital images respectively depicting a tissue sample of a second cohort of patients having a tumor known to be untreatable by said drug;
    for each of the received first digital images, performing, by the image analysis system:
        analyzing the first digital image for identifying first tumor cells in a region of said first image;
        analyzing said first image for identifying first FAP+ areas in said region, each first FAP+ area being a pixel blob representing one or more fibroblast expressing FAP
        analyzing said first image for identifying first distances between the identified first tumor cells and their respective nearest FAP+ area;
        computing a first proximity measure as a function of the identified first distances;
    for each of the received second digital images, performing, by the image analysis system:
        analyzing the second digital image for identifying second tumor cells in a region of said second image;
        analyzing said second image for identifying second FAP+ areas in said region, each second FAP+ area being a pixel blob representing one or more fibroblast expressing FAP;
        analyzing said second image for identifying second distances between the identified second tumor cells and their respective nearest FAP+ area;
        computing a second proximity measure as a function of the identified second distances;
    processing the first proximity measures in association with a "treatable" class membership tag and processing the second proximity measures in association with an "untreatable" class membership tag by an untrained classifier for generating a trained classifier, the trained classifier being configured to indicate, upon receiving a proximity measure for a slide of a further patient as input, if the tumor of the further patient can effectively be treated by a drug or drug-component that binds to FAP.

17. The image analysis method of claim 6, the predefined distance being in the range of 45 µm to 55 µm.

* * * * *